(12) United States Patent
Bryson

(10) Patent No.: US 6,454,086 B1
(45) Date of Patent: Sep. 24, 2002

(54) CLEANING AND STORING DEVICE FOR A PROPHYLACTIC

(76) Inventor: Timothy Bryson, 4611 Harwood Rd., Greensboro, NC (US) 27406

( * ) Notice: Subject to any disclaimer, the term of this patent is extended or adjusted under 35 U.S.C. 154(b) by 47 days.

(21) Appl. No.: 09/671,893

(22) Filed: Sep. 28, 2000

(51) Int. Cl.[7] .............................................. B65D 85/14
(52) U.S. Cl. ......................... 206/69; 206/209; 206/207
(58) Field of Search .......................... 206/69, 209, 207, 206/233, 438, 812

(56) References Cited

U.S. PATENT DOCUMENTS

| | | | |
|---|---|---|---|
| 3,970,215 A | * | 7/1976 | McLaren et al. ............. 221/45 |
| 4,974,730 A | | 12/1990 | Deruysscher |
| 5,152,996 A | | 10/1992 | Corey et al. |
| 5,244,096 A | | 9/1993 | Stoner |
| D368,026 S | | 3/1996 | Fields |
| 5,524,759 A | * | 6/1996 | Herzberg et al. ............ 206/494 |
| 5,638,949 A | * | 6/1997 | Jones .......................... 206/69 |
| 5,651,374 A | | 7/1997 | Wester |
| 5,664,677 A | * | 9/1997 | O'Connor .................... 206/494 |
| 5,666,972 A | | 9/1997 | Gifford |
| 5,862,908 A | * | 1/1999 | Arbin .......................... 206/69 |

* cited by examiner

Primary Examiner—Mickey Yu
Assistant Examiner—Troy Arnold

(57) ABSTRACT

A cleaning and storing device for a prophylactic for storing a prophylactic before and after use and for storing a cleaning member before and after it is used. The cleaning and storing device for a prophylactic includes a cleaning and storing device comprising an enclosure. The enclosure includes a front wall and a back wall, a first side wall, a second side wall, a third side wall and a fourth side wall. The cleaning and storing device also includes a cleaning member. The cleaning member comprises a panel. The panel comprising a porous material is positioned in the housing. In an embodiment the prophylactic is positioned generally in the enclosure.

6 Claims, 2 Drawing Sheets

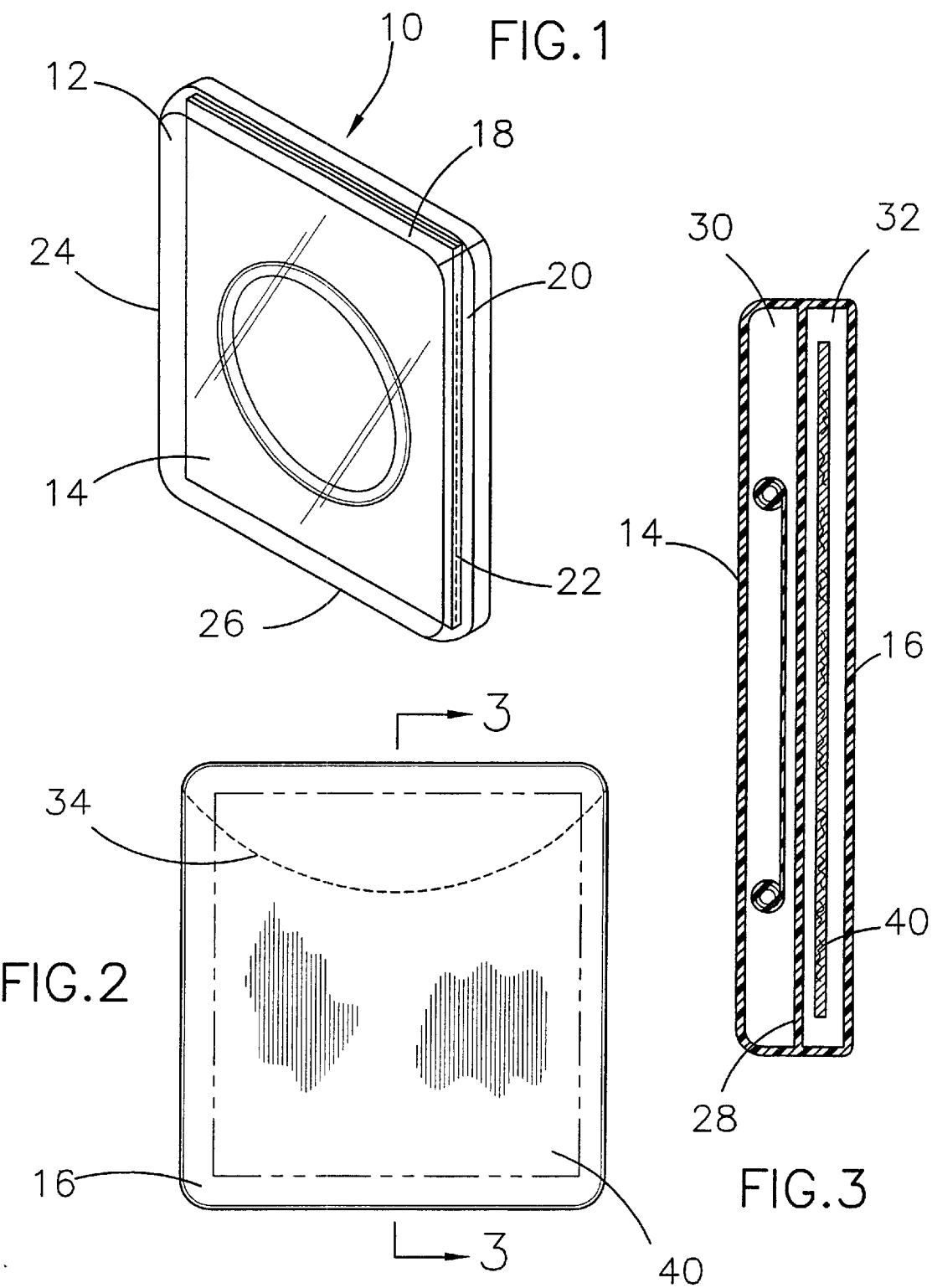

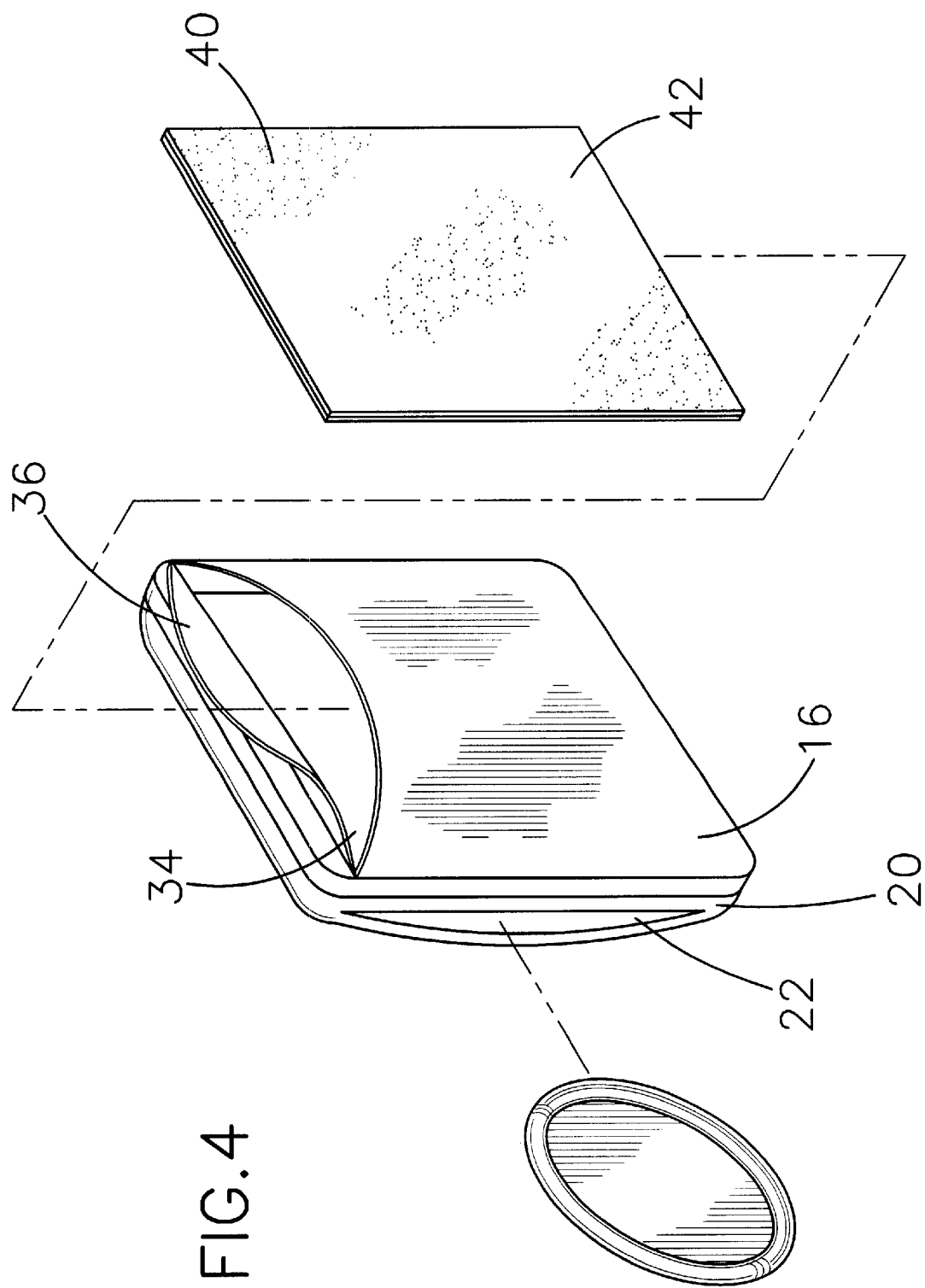

CLEANING AND STORING DEVICE FOR A PROPHYLACTIC

BACKGROUND OF THE INVENTION

1. Field of the Invention

The present invention relates to storing devices and more particularly pertains to a new a cleaning and storing device for a prophylactic for storing a prophylactic before and after use and for storing a cleaning member before and after it is used.

2. Description of the Prior Art

The use of storing devices is known in the prior art. More specifically, storing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,974,730; U.S. Pat. No. 5,152,996; U.S. Pat. No. 5,244,096; U.S. Pat. No. 5,666,972; U.S. Pat. No. 5,651,374; U.S. Pat. No. Des. 368,026.

While these devices fulfill their respective, particular objectives and requirements, the aforementioned patents do not disclose a new cleaning and storing device for a prophylactic. The inventive device includes an enclosure, said enclosure having a front wall and a back wall, a first side wall, a second side wall, a third side wall and a fourth side wall; a cleaning member, said cleaning member comprising a panel, said panel comprising a porous material said panel being positioned in said housing; and wherein the prophylactic is positioned generally in said enclosure.

In these respects, the a cleaning and storing device for a prophylactic according to the present invention substantially departs from the conventional concepts and designs. of the prior art, and in so doing provides an apparatus primarily developed for the purpose of storing a prophylactic before and after use and for storing a cleaning member before and after it is used.

SUMMARY OF THE INVENTION

In view of the foregoing disadvantages inherent in the known types of storing devices now present in the prior art, the present invention provides a new a cleaning and storing device for a prophylactic construction wherein the same can be utilized for storing a prophylactic before and after use and for storing a cleaning member before and after it is used.

The general purpose of the present invention, which will be described subsequently in greater detail, is to provide a new a cleaning and storing device for a prophylactic apparatus and method which has many of the advantages of the storing devices mentioned heretofore and many novel features that result in a new a cleaning and storing device for a prophylactic which is not anticipated, rendered obvious, suggested, or even implied by any of the prior art storing devices, either alone or in any combination thereof.

To attain this, the present invention generally comprises a cleaning and storing device for a prophylactic. The cleaning and storing device comprising an enclosure. The enclosure includes a front wall and a back wall, a first side wall, a second side wall, a third side wall and a fourth side wall. The cleaning and storing device also includes a cleaning member. The cleaning member comprises a panel. The panel comprising a porous material is positioned in the housing. In an embodiment the prophylactic is positioned generally in the enclosure.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new a cleaning and storing device for a prophylactic apparatus and method which has many of the advantages of the storing devices mentioned heretofore and many novel features that result in a new a cleaning and storing device for a prophylactic which is not anticipated, rendered obvious, suggested, or even implied by any of the prior art storing devices, either alone or in many combination thereof.

It is another object of the present invention to provide a new a cleaning and storing device for a prophylactic which may be easily and efficiently manufactured and marketed.

It is a further object of the present invention to provide a new a cleaning and storing device for a prophylactic, which is of a durable and reliable construction.

An even further object of the present invention is to provide a new a cleaning and storing device for a prophylactic which is susceptible of a low cost of manufacture with regard to both materials and labor, and which accordingly is then susceptible of low prices of sale to the consuming public, thereby making such a cleaning and storing device for a prophylactic economically available to the buying public.

Still yet another object of the present invention is to provide a new a cleaning and storing device for a prophylactic which provides in the apparatuses and methods of the prior art some of the advantages thereof while simultaneously overcoming some of the disadvantages normally associated therewith.

Still another object of the present invention is to provide a new a cleaning and storing device for a prophylactic for storing a prophylactic before and after use and for storing a cleaning member before and after it is used.

Yet another object of the present invention is to provide a new a cleaning and storing device for a prophylactic which includes a cleaning and storing device comprising an enclosure. The enclosure includes a front wall and a back wall, a first side wall, a second side wall, a third side wall and a fourth side wall. The cleaning and storing device also includes a cleaning member. The cleaning member comprises a panel. The panel comprising a porous material is positioned in the housing. In an embodiment the prophylactic is positioned generally in the enclosure.

Still yet another object of the present invention is to provide a new a cleaning and storing device for a prophylactic that provides a means of carrying the prophylactic with a cleaning member in a single package.

Even still another object of the present invention is to provide a new a cleaning and storing device for a prophylactic that provides a convenient means of disposing the prophylactic and the cleaning member after they have been used.

A further object of the present invention is to provide a new cleaning and storing device for a prophylactic that will provide reduce the effectiveness of a prophylactic due to being carried by another means such as within a wallet.

Yet another object of the present invention is to provide a new cleaning and storing device for a prophylactic that provides a hygienic cleaning member that may be used in conjunction with the condom or by itself.

These together with other objects of the invention, along with the various features of novelty which characterize the invention, are pointed out with particularity in the claims annexed to and forming a part of this, disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a new cleaning and storing device for a prophylactic according to the present invention.

FIG. 2 is a schematic perspective view of the present invention showing the back wall and the cleaning member positioned in the second portion.

FIG. 3 is a schematic side view of the present invention showing the condom in the first portion and the cleaning member in the second portion with the two being separated by an intermediate wall.

FIG. 4 is a schematic perspective view of the present invention showing the removal and replacement of a condom and the cleaning member.

DESCRIPTION OF THE PREFERRED EMBODIMENT

With reference now to the drawings, and in particular to FIGS. 1 through 4 thereof, a new cleaning and storing device for a prophylactic embodying the principles and concepts of the present invention and generally designated by the reference numeral 10 will be described.

As best illustrated in FIGS. 1 through 4, the cleaning and storing device for a prophylactic 10 generally an enclosure 12. The enclosure 12 includes a front wall 14 and a back wall 16, a first side wall 18, a second side wall 20, a third side wall 24 and a fourth side wall 26. There is an intermediate wall 28 positioned generally between the front and back walls 14 and 16 and integrally coupled to and extending between each of the side walls such that a first portion 30 and a second portion 32 of the enclosure 12 are defined. The second side wall 20 includes a perforation 22 positioned generally between the front wall 14 and the intermediate wall 28. The perforation 22 includes a length parallel to a length of the third side wall 24. The perforation provides a means of accessing the condom within the first portion 30 of the enclosure 12. The back wall 16 of the enclosure 21 includes an elongated slit 34 therein such that a flap 36 is defined. The flap 36 is positioned generally adjacent to the first side wall 18 of the enclosure 12. The flap 36 provides a means for accessing the second portion 32 of the enclosure 12. The enclosure 12 comprises a resiliently flexible material. Any resiliently flexible material may be used such as plastic or cloth.

The cleaning and storing device for a prophylactic 10 also includes a cleaning member 40. The cleaning member 40 comprises a panel 42. The panel 42 comprises a generally porous material such as cotton or a synthetic fiber having porous characteristics. The panel 42 is position generally between the intermediate wall 28 and the back wall 16 in the second portion 32 of the enclosure 12.

An anti-bacterial solution generally saturates the panel. The anti-bacterial solution that saturates the panel is a conventional solution currently being used in the art.

In an embodiment, the prophylactic is positioned generally between the intermediate wall 28 and the front wall 14 in the first portion 30 of the enclosure 12.

In use, the perforation 22 in the second side wall 20 is opened and the condom is removed from the first portion 30 of the enclosure 12. After the condom has been used it may be placed in the first portion 30 of the enclosure 12 for disposal. The cleaning member 40 may then be removed from the second portion 32 through the elongated slit 34 in the back wall 16. The cleaning member 40 may then be placed back in the second portion 32 of the enclosure 12 after it has been used. The entire enclosure 12 may then be disposed.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art,it is not desired to limit the invention to the exact construction and operation shown and described, and accordingly, all suitable modifications and equivalents may be resorted to, falling within the scope of the invention.

I claim:

1. A cleaning and storing device for a prophylactic, said cleaning and storing device comprising:

an enclosure, said enclosure having a front wall and a back wall, a first side wall, a second side wall, a third side wall and a fourth side wall;

a cleaning member, said cleaning member comprising a panel, said panel comprising a porous material said panel being positioned in said enclosure;

wherein a prophylactic is positioned in said enclosure; and said back wall of said enclosure having an elongated slit therein such that a flap is defined, said flap being positioned generally adjacent to said first side wall of said enclosure;

said enclosure having an intermediate wall being positioned generally between said front and back walls and integrally coupled to and extending between each of said first, second, third and fourth side walls such that a first portion and a second portion of said enclosure are defined; and said panel being positioned generally between said intermediate wall and said back wall in said second portion of said enclosure.

2. The cleaning and storing device of claim 1, wherein said second side wall having a perforation being positioned generally therein between said front wall and said back wall, said perforation having a length parallel to a length of said third wall.

3. The cleaning and storing device of claim 2, wherein said second side wall further comprises:

said second side wall having a perforation therein being positioned generally between said front wall and said intermediate wall, said perforation having a length parallel to a length of said third wall.

4. The cleaning and storing device of claim 1, wherein said enclosure further comprises:

said enclosure comprising a resiliently flexible material.

5. The cleaning and storing device of claim 1, further comprising:

an anti-bacterial solution, said anti-bacterial solution generally saturating said panel.

6. A cleaning and storing device for a prophylactic, said cleaning and storing device comprising:

an enclosure, said enclosure having a front wall a back wall, a first side wall, a second side wall, a third side wall and a fourth side wall, an intermediate wall being positioned generally between said front and back walls and integrally coupled to and extending between each of said side walls such that a first portion and a second portion of said enclosure are defined, said second side wall having a perforation being positioned generally between said front wall and said intermediate wall, said perforation having a length parallel to a length of said third wall, said back wall of said enclosure having an elongated slit therein such that a flap is defined, said flap being positioned generally adjacent to said first side wall of said enclosure, said enclosure comprising a resiliently flexible material;

a cleaning member, said cleaning member comprising a panel, said panel comprising a porous material said panel being position generally between said intermediate wall and said back wall in said second portion of said enclosure;

an anti-bacterial solution, said anti-bacterial solution generally saturating said panel; and wherein a prophylactic is positioned between said intermediate wall and said front wall in said first portion of said enclosure.

* * * * *